United States Patent [19]

Schmierer et al.

[11] Patent Number: 4,808,213
[45] Date of Patent: Feb. 28, 1989

[54] 2,3,6-SUBSTITUTED PHENYLIMIDAZOLE DERIVATIVES AND THE USE THEREOF AS GROWTH REGULATORS

[75] Inventors: Roland Schmierer, Todtenweis; Hilmar Mildenberger, Kelkheim; Helmut Bürstell, Frankfurt am Main, all of Fed. Rep. of Germany

[73] Assignee: Hoechst Aktiengesellschaft, Frankfurt am Main, Fed. Rep. of Germany

[21] Appl. No.: 89,476

[22] Filed: Aug. 25, 1987

[30] Foreign Application Priority Data

Aug. 27, 1986 [DE] Fed. Rep. of Germany ....... 3629064

[51] Int. Cl.$^4$ .................... A01N 43/48; C07D 233/66
[52] U.S. Cl. .......................................... 71/92; 548/343
[58] Field of Search ........................... 548/343; 71/92

[56] References Cited

FOREIGN PATENT DOCUMENTS 1201716 5/1982 Canada .............................. 548/343
3217094 5/1982 Fed. Rep. of Germany ...... 548/343

Primary Examiner—Alan L. Rotman
Assistant Examiner—Robert C. Whittenbaugh
Attorney, Agent, or Firm—Curtis, Morris & Safford

[57] ABSTRACT

The compounds of the formula I, or salts thereof,

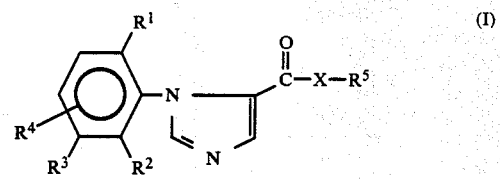

in which
$R^1$ and $R^2$, independently of one another, denote $(C_1-C_4)$-alkyl,
$R^3$ denotes halogen, in particular Cl or Br,
$R^4$ denotes hydrogen, Cl, Br or methyl,
X denotes O, S or N-$R^5$, and
$R^5$ denotes hydrogen, $(C_2-C_6)$-alkenyl or $(C_1-C_6)$-alkyl, where the alkyl group may be up to disubstituted by $(C_1-C_6)$-alkoxy or $(C_1-C_3)$-dialkylamino, or up to hexasubstituted by halogen, have an excellent plant growth-regulating action in important crops.

4 Claims, No Drawings

2,3,6-SUBSTITUTED PHENYLIMIDAZOLE DERIVATIVES AND THE USE THEREOF AS GROWTH REGULATORS

DE-A No. 3,217,094 discloses 1-phenylimidazole-5-carboxylic acid derivatives and the use thereof as fungicides, herbicides and plant growth regulators.

Surprisingly, it has now been found that selected imidazole compounds which are substituted by halogen in the 3-position of the phenyl ring have a particularly intensive growth-regulating action.

The present invention therefore relates to compounds of the formula I

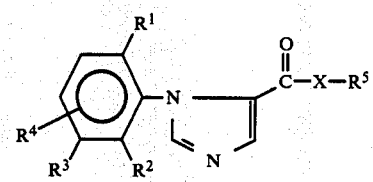

in which
$R^1$ and $R^2$, independently of one another, denote $(C_1-C_4)$-alkyl,
$R^3$ denotes halogen, in particular Cl or Br,
$R^4$ denotes hydrogen, Cl, Br or methyl,
X denotes O, S or $N-R^5$, and
$R^5$ denotes hydrogen, $(C_2-C_6)$-alkenyl or $(C_1-C_6)$-alkyl, where the alkyl group may be up to disubstituted by $(C_1-C_6)$-alkoxy or $(C_1-C_3)$-dialkylamino, or up to hexasubstituted by halogen,
and the salts and quaternization products thereof which are acceptable for agricultural purposes.

Possible halogenated $(C_1-C_6)$alkyl for $R^5$ are, in particular, the hexafluoropropyl, 2,2,3,3-tetrafluoropropyl, 2,2,2-trifluoroethyl, 2,2,2-trichloroethyl and 2,2,3,4,4,4-hexafluorobutyl radicals.

Salt formation or quaternization occurs either at the —COOH or (C=O)-SH group (X=O or S; $R^5$=H) or at the basic nitrogen atom of the imidazole ring. Salt formation or quaternization at the imidazole ring is not possible when $R^5$ contains a cation. Halogen is taken to mean F, Cl, Br or I, in particular F, Cl or Br.

All inorganic or organic acids which are capable, as a consequence of their pKs value, of forming salts, for example hydrohalic acids, nitric acid, sulfuric acid, phosphoric aicd, phosphonic acids, sulfonic aicds, haloacetic acids or oxalic acid, are suitable for the salts.

Possible cations which can be employed in agriculture are metal cations, for example alkali metal or alkaline earth metal cations, such as Na, K or Mg, or ammonium, or organic cations, such as, for example, ammonium, phosphonium, sulfonium or sulfoxonium ions which are substituted by organic radicals, or optionally substituted hydrazonium, hydroxylammonium, guanidinium or aminoguanidinium.

Organically substituted ammonium denotes primary, secondary, tertiary or quaternary, aliphatic, aromatic or heteroaromatic ammonium which may contain 1 to three nitrogen atoms. The nitrogen atoms of the amine can in this case also be part of a cyclic system. Examples of such ammonium salts which may be mentioned are: mono-, di-, tri- and tetra[$(C_1-C_6)$alkyl]ammonium, such as isopropylammonium, butylammonium, stearylammonium, triethylammonium, mono-, di- and tri-[$(C_1-C_4)$alkoxy$(C_1-C_4)$alkyl]ammonium or mono-, di- and tri-[$(C_1-C_6)$alkanol]ammonium, such as methoxyethylammonium, methoxypropylammonium, triethanolammonium or tripropanolammonium, or ammonium compounds containing mixed radicals, such as tert.-butyldiethanolammonium, triethylenebenzylammonium, hydroxyethyltrimethylammonium or chloroethyltrimethylammonium; or allylammonium, diallylammonium, cyclohexylammonium, menthylammonium, aminoethylammonium, ethylenediammonium, benzohydrylammonium, pyrrolidinium, morpholinium, 3-pyridylammonium, piperidinium or piperazinium, or ammonium which is derived from an amino acid or an ester thereof, such as $\oplus NH_3-CH_2-COOCH_3$.

Corresponding radicals as in the case of ammonium can be present in the other abovementioned organic cations.

The invention furthermore relates to processes for the preparation of compounds of the formula I and the salts or quaternization products thereof, wherein
(a) a tantomeric bisformyl ester of the formula (IIa) or (IIb)

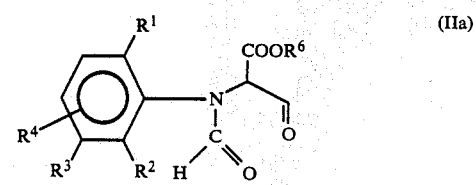

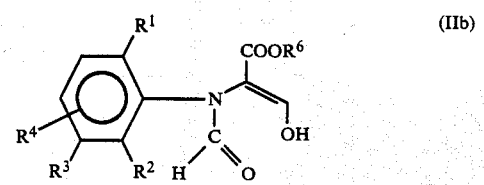

in which $R^6$ denotes $(C_1-C_{12})$-alkyl, is heated in the presence of ammonia or a compound which liberates ammonia, or (b) an aminophenyl derivative of the formula III

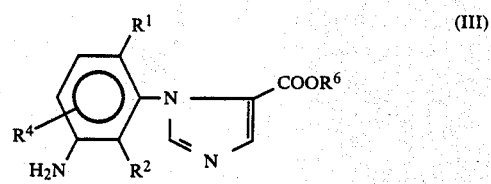

is diazotized and subsequently reacted with a halide in accordance with the Sandmeyer reaction, or (c) in the case where $R^3$ represents chlorine or bromine, a phenylimidazole derivative of the formula IV

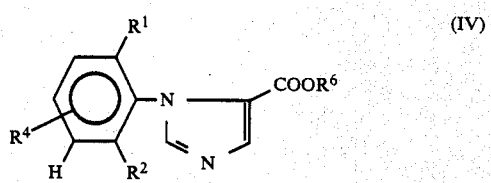

is brominated or chlorinated, or the compounds obtained under (a), (b) or (c) are derivatized.

In the derivatization, the —COOR⁶ radical is modified in a known fashion, for example by saponification, esterification, transesterification, amidation or salt formation, as described, for example, in Patent Applications DE-A Nos. 3,444,918 and 3,442,690, or salt formation or quaternization takes place at the basic nitrogen atom of the imidazole ring.

Concerning (a) The formyl compounds IIa/IIb can be prepared from the corresponding anilines by known processes, as described, for example, in DE-A No. 3,217,094. The formyl compounds are cyclized in the presence of ammonia or substances which form ammonia when heated, such as, for example, ammonium acetate, ammoniumbenzoate or formamide, or in the presence of highboiling solvents, such as, for example, xylene or formamide, at temperatures from 100° to 200° C.

Concerning (b) The amino compounds are accessible from the known imidazoles of the formula IV (DE-A No. 3,217,094) by nitration and reduction. The Sandmeyer reaction can be carried out in good yields under conventional reaction conditions (cf., for example, Organikum, VEB Deutscher Verlag der Wissenschaften Berlin 1973, pp. 590 ff).

Concerning (c) The halogenation can likewise be carried out from the known compounds of the formula IV by conventional processes (cf., for example, Organikum, see above, pp. 342 ff).

The salts of the compounds of the formula (I) can be obtained in a simple fashion by conventional salt-formation methods, for example by dissolving a compound of the formula (I) in a suitable organic solvent and adding the acid, and can be purified in a known fashion, for example by filtering off, isolating and optionally washing with an inert organic solvent.

The compounds according to the invention can achieve typical growth-regulating effects which—compared to the compounds known from DE-A No. 3,217,094—can surprisingly be achieved even at very low dosages.

The compounds according to the invention engage in a regulating manner in the plant's own metabolism and can therefore be employed to influence plant constituents in a specific manner and to simplify harvesting, such as for initiating desiccation and growth inhibition. In addition, they are suitable for general control and inhibition of undesired vegetative growth, without at the same time destroying the plants. Inhibition of vegetative growth plays a major part in many mono- and dicotyledon crops since lodging can thereby be reduced or completely prevented. The growth-regulating activity of the compounds as growth inhibitors in cereals, corn, soybean, tobacco, cotton, horse beans, rape, rice, sunflowers and turf, and their ability to increase the content of desired constituents such as carbohydrates (for example sugar cane or millet crops) and protein in crop plants should be particularly emphasized.

When used in practice, the compounds according to the invention can also, if appropriate, be advantageously combined with known growth regulators. Such known growth regulators are the compounds of the formula (V)

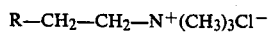   (V)

in which R denotes OH or Cl (common name chlormequat for R=Cl), furthermore, N,N-dimethylpiperidinium chloride (VI; common name: mepiquat chloride), α-cyclopropyl-4-methoxy-α-(pyrimidin-5-yl)benzyl alcohol (VIII; common name: ancymidol), (3aα, 4β, 4aα, 6aα, 7β, 7aα)-1-(4-chlorophenyl)-3a, 4, 4a, 6a, 7, 7a-hexahydro-4,7-methano1H-[1,2]diazeto[3,4-f]benzotriazole (VIII; common name: tetcylacis), 2,2-dimethylsuccinomonohydrazide (IX, common name: diaminoazide), 6-hydroxy-2H-pyridazin-3-one (X, maleic anhydride), 2-chloro-9-hydroxy-9H-fluorene-9-carboxylic acid (XI, chlorflurenol), N-[2,4-dimethyl-5-[[(trifluoromethyl)sulfonyl]amino]phenyl]acetamide (mefluidide) and 2-chloroethylphosphonic acid (XIII, ethephon).

The growth-regulating actions of the compounds of the formulae (V) to (XIII) are described in Plant Growth Regulator Handbook of the Plant Growth Regulator Working Group, 2nd Ed., 1981.

In place of the compounds of the formulae (V) and (VI), comparable salts which contain another conventional anion, such as bromide, nitrate or ½ sulfate, in place of the chloride ion, can be employed in principle.

Combinations can exist both as mixed formulations of the components, which are then used diluted with water in a conventional fashion; or they can be prepared as so-called tank mixes by common dilution with water of the separately formulated components; it is also possible to use the components in succession, i.e. the components are then applied in individual formulations.

The compounds of the general formula (I) may also be combined with natural or vegetative hormones, such as auxins or cytokinins.

A further solution of the object set are also plant growth-regulating agents which are distinguished by an active content of at least one of the compounds according to the invention.

The compounds according to the invention can be applied in conventional preparations, if appropriate mixed with further active components, such as wettable powders, emulsifiable concentrates, sprayable solutions, dusts, dispersions, granules or microgranules.

Wettable powders are preparations which are uniformly dispersible in water and which contain, besides the active compound(s) and in addition to any diluent or inert material, wetting agents, such as polyoxyethylated fatty alcohols, alkylsulfonates or alkylphenylsulfonates, and/or dispersants, such as sodium lignin-sulfonate, sodium 2,2'-dinaphthylmethane-6,6'-disulfonate, sodium dibutylnaphthalenesulfonate or sodium oleoylmethyltaurinate. The preparation is carried out in the conventional fashion, for example by grinding and mixing the components.

Emulsifiable concentrates can be prepared, for example, by dissolving the active ingredients in an inert, organic solvent, such as butanol, cyclohexanone, dimethylformamide, xylene or higher-boiling aromatics or aliphatic or cycloaliphatic hydrocarbons, with addition of one or more emulsifiers. In the case of liquid active ingredients, the solvent component can also be omitted entirely or partly. As emulsifiers, the following can be used, for example: calcium salts of alkylarylsulfonates, such as Ca dodecylbenzenesulfonate, or non-ionic emulsifiers, such as fatty acid polyglycol esters, alkylaryl polyglycol esters, fatty alcohol polyglycol ethers, propylene oxide/ethylene oxide condensation products, fatty alcohol/propylene oxide condensation products, alkyl polyglycol ethers, sorbitan fatty acid esters, polyoxyethylene sorbitan fatty acid esters or polyoxyethylene sorbitol esters.

Dusts can be obtained by grinding the active ingredients with finely divided solid substances, for example talcum, natural clays, such as kaolin, bentonite or pyrophillite, or diatomaceous earth. Granules can be prepared either by atomizing the active ingredients onto adsorptive, granulated inert material or by applying active ingredient concentrates onto the surface of carrier materials, such as sand or kaolinites, or of granulated inert material by means of binders, for example polyvinyl alcohol or sodium polyacrylate, or alternatively mineral oils. Suitable active ingredients can also be granulated—if desired as a mixture with fertilizers—in the fashion which is conventional for the preparation of fertilizer granules.

In wettable powders, the active compound concentration is about 5 to 90% by weight, and the remainder to 100% by weight comprises conventional formulation components. In the case of emulsifiable concentrates, the active ingredient concentration can be about 3 to 80% by weight. Dust-form formulations usually contain 0.025 to 20% by weight of active ingredient(s), and sprayable solutions about 2 to 20% by weight. In the case of granules, the active ingredient content depends partly on whether the active compound is liquid or solid and which granulation auxiliaries, fillers etc. are used. In addition, the active ingredient formulations mentioned contain, if appropriate, the adhesives, wetting agents, dispersants, emulsifiers, penetrants, solvents, fillers or excipients which are conventional in each case.

For use, the concentrates, present in commercially available form, are diluted, if appropriate, in a conventional fashion, for example using water in the case of wettable powders, emulsifiable concentrates, dispersions and, in some cases, also in the case of microgranules. Dust-form and granulated preparations and sprayable solutions are not usually diluted with further inert substances before application.

The application rate of the compounds according to the invention generally varies between 0.02 and 2.5 kg of active substance per hectare, preferably 0.05 to 1.5 kg/ha.

The examples below are intended to illustrate the invention.

FORMULATION EXAMPLES

Example 1

A dusting agent is obtained by mixing (a) 10 PW[(1)] of active ingredient with 90 PW of talcum or another inert substance and comminuting in a hammer mill, or by (b) homogenizing 60 PW of active ingredient, 35 PW of talcum and 5 PW of adhesive (for example a polysaccharide such as ®Rhodopol supplied by Rhone-Poulenc S.A.) in the same fashion.
(1) PW=parts by weight

Example 2

A wettable powder which is easily dispersible in water is obtained by mixing 25 PW of active ingredient, 64 PW of kaolin-containing quartz as inert material, 10 PW of potassium ligninsulfonate and 1 PW of sodium oleoylmethyltaurinate as wetting agent and dispersant, and grinding in a pin disk mill. A formulation containing 5% of active ingredient can be composed as follows: 5% of active ingredient, 6% of a sulfonated naphthalene-formaldehyde condensate (for example ®Dispersogen A supplied by Hoechst AG), 2% of an Na salt of an alkylnaphthalenesulfonic acid (for example ®Leonil DB supplied by Hoechst AG), 5% of a mixture of polypropylene glycol and $SiO_2$ (for example ®Acrotin 341 supplied by Hoechst AG), 25% of a silicate (for example ®Sipernat supplied by Degussa AG) and 57% of kaolin type 1777.

Example 3

A dispersion concentrate which is easily dispersible in water is obtained by mixing 20 PW of active ingredient with 6 PW of an alkylphenol polyglycol ether (for example ®Triton X 207 supplied by Rohm and Haas Co.), 3 PW of isotridecanol polyglycol ether (8 ethylene oxide units) and 71 PW of paraffinic mineral oil (boiling range about 255 to above 377° C.), and grinding in a ball mill to a fineness of below 5 μm.

Example 4

An emulsifiable concentrate is obtained from 15 PW of active ingredient(s), 75 PW of cyclohexanone as solvent and 10 PW of oxyethylated nonylphenol (10 ethylene oxide units) as emulsifiers.

CHEMICAL EXAMPLES

Example 1

Ethyl 1-(3-chloro-6-ethyl-2-methylphenyl)-imidazole-5-carboxylate 19.2 g (0.068 mol) of ethyl 2-(3-chloro-6-ethyl-2-methyl-N-formylanilino)-3-hydroxy-acrylate were heated to an internal temperature of 153° C. with 12.3 g (0.088 mol) of ammonium benzoate in 100 ml of xylene with removal of the xylene/water mixture by distillation. The mixture was allowed to cool and was taken up in toluene, and the organic phase was washed twice with 2N sodium hydroxide solution and twice with water, dried over sodium sulfate and evaporated. 15.2 g (85% of theory) of ethyl 1-(3-chloro-6-ethyl-2-methylphenyl)-imidazole-5-carboxylate were obtained as a pale brown oil. Identification was effected by $^1$H NMR spectroscopy.

Example 2

Ethyl 1-(3-bromo-2,6-diethylphenyl)-imidazole-5-carboxylate 20 g (0.07 mol) of ethyl 1-(3-amino-2,6-diethylphenyl)imidazole-5-carboxylate were added to a mixture of 30 ml of concentrated hydrobromic acid, 30 ml of glacial acetic acid and 30 ml of water, the mixture was cooled to 0° C., and a solution of 12.0 g (0.17 mol) of sodium nitrite in 15 ml of water was added dropwise at this temperature. After 30 minutes at 0° C., the excess nitrite was decomposed using urea, and the solution was added dropwise at 0° C. to a copper bromide solution (prepared by conventional processes from 24.9 g of copper sulfate, 15.5 g of sodium bromide, 6.3 g of sodium sulfite, 80 ml of water and 40 ml of concentrated hydrobromic acid). The reaction mixture was allowed to warm to room temperature and was neutralized, the product was extracted with methylene chloride, and the organic phase was washed with water, dried over sodium sulfate and evaporated. After chromatographic purification, 17.4 g (71% of theory) of ethyl 1-(3-bromo-2,6-diethylphenyl)-imidazole-5-carboxylate were obtained as a pale yellow oil. Identification was effected by ¹H NMR spectroscopy.

Example 3

1-(3-Bromo-2,6-diethylphenyl)-imidazole-5-carboxylic acid 17.4 g of the ethyl ester described in Example 2 were heated for 1 hour at 80° C. with 150 ml of 2N sodium hydroxide solution. After cooling, the mixture was acidified to pH 3 using concentrated hydrochloric acid, and the colorless solid was filtered off under suction. After drying, 11.6 g (72% of theory) of 1-(3-bromo-2,6-diethylphenyl)-imidazole-5-carboxylic acid of melting point 224°–7° C. were obtained.

The following examples can be prepared by the process described above.

When Y represents radicals other than —COOCH$_3$ and —COOC$_2$H$_5$ in Table 1, these were prepared from the appropriate esters by conventional, generally known processes, such as, for example, saponification (Example 3), subsequent preparation of the acyl chloride and reaction with alcohols, amines or thiols; or reaction of the acid with bases for salt formation.

TABLE 1

Imidazole derivatives

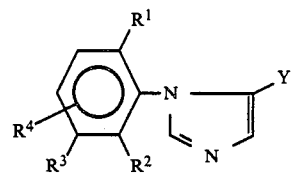

| Example No. | R¹ | R² | R³ | R⁴ | Y | m.p./b.p. (°C.) |
|---|---|---|---|---|---|---|
| 4 | CH$_3$ | CH$_3$ | Br | H | —COOCH$_3$ | 132–5 |
| 5 | " | " | " | " | —COOH | 227–9 |
| 6 | " | " | " | " | —COO$^\ominus$.NH$_4^\oplus$ | |
| 7 | " | " | " | " | —C(=O)S—C$_2$H$_5$ | |
| 8 | " | " | " | " | —C(=O)S—CH$_3$ | |
| 9 | " | C$_2$H$_5$ | Cl | " | —COOH | 179–82 |
| 10 | " | " | " | " | —COOK | |
| 11 | " | " | " | " | —COO.½Mg | |
| 12 | " | " | " | " | —COOCH$_3$ | 101 |
| 13 | " | " | " | " | —COOC$_2$H$_5$ | 135–7/0.01 torr |
| 14 | " | " | " | " | —C(=O)NH$_2$ | 168–72 |
| 15 | " | " | " | " | —C(=O)i-NH—C$_4$H$_9$ | |
| 16 | " | " | " | " | —C(=O)—NHCH$_3$ | 209–13 |
| 17 | " | " | " | " | —C(=O)N(CH$_3$)$_2$ | oil |
| 18 | " | " | " | " | —C(=O)NH—(CH$_2$)$_3$—OCH$_3$ | |
| 19 | " | " | " | " | —C(=O)N(CH$_3$)—CH(CH$_3$)$_2$ | |
| 20 | " | " | " | " | —COOCH$_2$—CCl$_3$ | |
| 21 | " | " | " | " | —C(=O)NH—CH$_2$—CH=CH$_2$ | |
| 22 | " | " | " | " | —COOCH$_3$ (Hydrochloride) | |
| 23 | C$_2$H$_5$ | CH$_3$ | " | " | —COOH | 185–92 |
| 24 | " | " | " | " | —COO$^-$.[N(C$_2$H$_5$)$_4$]$^+$ | |
| 25 | " | " | " | " | —COO$^-$.H$_2$N$^\oplus$⟨C$_6$H$_{11}$⟩ | |
| 26 | " | " | " | " | —COONa | |
| 27 | " | " | " | " | —COO$^\ominus$.S$^\oplus$(CH$_3$)$_3$ | |
| 28 | " | " | " | " | —COOCH$_3$ | 105–10 |
| 29 | " | " | " | " | —COO—i-C$_3$H$_7$ | oil |
| 30 | " | " | " | " | —COOC$_6$H$_{13}$ | |
| 31 | " | " | " | " | —COO—(CH$_2$)$_2$—O—C$_2$H$_5$ | |
| 32 | " | " | " | " | —COO—CH(CF$_3$)$_2$ | |
| 33 | " | " | " | " | —C(=O)NH$_2$ | 170 |
| 34 | " | " | " | " | —C(=O)N(—C$_2$H$_5$)$_2$ | oil |
| 35 | " | " | " | " | —C(=O)N(—CH$_3$)—CH(CH$_3$)$_2$ | |
| 36 | " | " | " | " | —C(=O)N(CH$_2$—CH=CH$_2$)$_2$ | |
| 37 | " | C$_2$H$_5$ | " | " | —COOH | 210–4 (decomp.) |
| 38 | " | " | " | " | —COONa | 144–8 |
| 39 | " | " | " | " | —COOK | 210–14 |
| 40 | " | " | " | " | —COO$^\ominus$[HN(—CH$_2$—CH$_2$—OH)$_3$]$^\oplus$ | 89–94 |
| 41 | " | " | " | " | —COO$^\ominus$[P$^\oplus$(CH$_3$)(Phenyl)$_3$] | |
| 42 | " | " | " | " | —COOH (Hydrochloride) | |
| 43 | " | " | " | " | —COOH(2-Chlorethyl-phosphonate | |
| 44 | " | " | " | " | —COOH (Sulfonate) | |
| 45 | " | " | " | " | COOCH$_3$ | |
| 46 | " | " | " | " | —COOC$_2$H$_5$ | 153–7/0.01 torr |
| 47 | " | " | " | " | —COOCH$_2$—CF$_3$ | |
| 48 | " | " | " | " | —COOCH$_2$—CHF—CF$_2$—CF$_3$ | |
| 49 | " | " | " | " | —COOCH$_2$—CH$_2$—N(C$_2$H$_5$)$_2$ | |
| 50 | " | " | " | " | —COO—n-C$_3$H$_7$ | oil |
| 51 | " | " | " | " | —COO—CH$_2$—CH=CH$_2$ | oil |

TABLE 1-continued

Imidazole derivatives

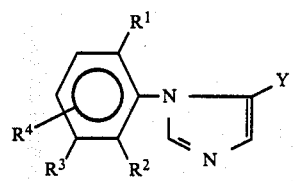

| Example No. | R¹ | R² | R³ | R⁴ | Y | m.p./b.p. (°C.) |
|---|---|---|---|---|---|---|
| 52 | " | " | " | " | —COO—n-$C_6H_{13}$ | |
| 53 | " | " | " | " | —COO—i-$C_3H_7$ | |
| 54 | " | " | " | " | —C(=O)—$NH_2$ | 188–93 |
| 55 | " | " | " | " | —C(=O)—NH—$CH_2$—CH($OCH_3$)$_2$ | 110–4 |
| 56 | " | " | " | " | —C(=O)—N($CH_3$)[$CH_2$—CH($OC_2H_5$)$_2$] | |
| 57 | " | " | " | " | —C(=O)NH-i-$C_3H_5$ | |
| 58 | " | " | " | " | —C(=O)NH—$CH_2$-i-$C_3H_7$ | |
| 59 | " | " | " | " | —C(=O)NH—$CH_3$ | 187–94 |
| 60 | " | " | " | " | —C(=O)N(—$CH_3$)$_2$ | oil |
| 61 | " | " | " | " | —C(=O)—SH | |
| 62 | " | " | " | " | —C(=O)S$C_2H_5$ | |
| 63 | " | " | " | 4-Br | —COOH | |
| 64 | " | " | " | " | —COO$C_2H_5$ | 70–6 |
| 65 | " | " | " | " | —COO—$CH_3$ | |
| 66 | " | " | " | " | —COO ½Ca | |
| 67 | " | " | " | 4-Br | .C(=O)$NH_2$ | |
| 68 | " | " | " | " | —C(=O)NH—n-$C_6H_{13}$ | |
| 69 | " | " | " | 4-$CH_3$ | —COOH | 213–5 |
| 70 | " | " | " | " | —COO$^{\ominus}$·$H_2N^{(+)}$⟨morpholine⟩ | resin |
| 71 | " | " | " | " | —COO$CH_3$ | oil |
| 72 | " | " | " | " | —COO$C_2H_5$ | oil |
| 73 | " | " | " | " | —COO($CH_2$)$_2$—O—$CH_3$ | |
| 74 | " | " | " | " | —C(=O)$NH_2$ | 163–5 |
| 75 | " | " | " | " | —C(=O)$NH_2$ (Hydrochloride) | |
| 76 | " | " | " | " | —C(=O)—NH—$C_4H_9$ | |
| 77 | " | " | " | 5-Cl | —COOH | 197–202 |
| 78 | " | " | " | " | —COO$^{\ominus}$[HN$^{(+)}$($C_2H_5$)$_2$] | |
| 79 | " | " | " | " | —COO$^{\ominus}$[Cl—$CH_2$—$CH_2$—N$^{\oplus}$($CH_3$)$_3$] | |
| 80 | " | " | " | " | —COO$CH_3$ | 32–4 |
| 81 | " | " | " | " | —COO$C_2H_5$ | 132–36 |
| 82 | " | " | " | " | —COO—CH($CH_3$)$C_6H_{13}$ | |
| 83 | " | " | " | " | —C(=O)$NH_2$ | 179–85 |
| 84 | " | " | " | " | —C(=O)NH—CH($CH_3$)$_2$ | |
| 85 | " | " | " | " | —C(=O)NH-i-$C_5H_{11}$ | |
| 86 | " | " | " | " | —C(=O)N($CH_3$)$CH_2CF_3$ | |
| 87 | " | " | F | H | —COOH | |
| 88 | " | " | " | " | —COO$CH_3$ | |
| 89 | " | " | " | " | —COO$C_2H_5$ | |
| 90 | " | " | " | " | —C(=O)$NH_2$ | |
| 91 | " | " | I | " | —COOH | 202–4 |
| 92 | " | " | " | " | —COO$C_2H_5$ | oil |
| 93 | " | " | Cl | " | —COOH | |
| 94 | " | " | " | " | —COO$C_2H_5$ | |
| 95 | " | " | " | " | —C(=O)$NH_2$ | |
| 96 | " | " | " | 5-$CH_3$ | —COOH | |
| 97 | " | " | " | " | —COO$C_2H_5$ | |
| 98 | " | " | " | " | —C=O)$NH_2$ | |
| 99 | " | " | " | " | —C=O)NH—$CH_3$ | |
| 100 | CH($CH_3$)$_2$ | CH($CH_3$)$_2$ | " | H | —COOH | |
| 101 | " | " | " | " | —COO$^{(-)}$[$H_3$N$^{(+)}$—$CH_2$COO$CH_3$] | |
| 102 | " | " | " | " | —COO$^{(-)}$./2Zn$^{(+)}$ | |
| 103 | " | " | " | " | —COO$CH_3$ | |
| 104 | " | " | " | " | —COO($CH_2$)$_2$—O—$C_4H_9$ | |
| 105 | " | " | " | " | —COOCH($CF_3$)$_2$ | |
| 106 | " | " | " | " | —C(=O)$NH_2$ | |
| 107 | " | " | " | " | —C(=O)N($CH_3$)$_2$ | |
| 108 | " | " | " | " | —C(=O)NH$CH_2$—CH=$CH_2$ | |
| 109 | " | " | " | " | —C(=O)NH$C_6H_{13}$ | |
| 110 | " | " | " | " | —C(=O)NH($CH_2$)$_3$—N($C_2H_5$)$_2$ | |
| 111 | $CH_3$ | $CH_3$ | Br | " | —COO$C_2H_5$ | 78–81 |
| 112 | " | " | " | " | —COO$C_3H_7$ | 100–5 |
| 113 | " | " | " | " | —COOCH($CF_3$)$_2$ | 92–5 |

TABLE 1-continued
Imidazole derivatives

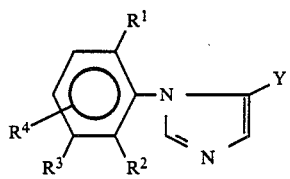

| Example No. | R¹ | R² | R³ | R⁴ | Y | m.p./b.p. (°C.) |
|---|---|---|---|---|---|---|
| 114 | " | " | " | " | —CONHCH₃ | 202-6 |
| 115 | " | " | " | " | —CON(CH₃)₂ | oil |
| 116 | " | " | " | " | —CONHCH(CH₃)₂ | 90-5 |
| 117 | " | C₂H₅ | Cl | " | —COO—CH(CH₃)₂ | 59-63 |
| 118 | " | " | " | " | —COO—CH(CF₃)₂ | oil |
| 119 | " | " | " | " | —COOCH₂—CH=CH₂ | oil |
| 120 | " | " | " | " | —CONHC₂H₅ | oil |
| 121 | " | C₂H₄ | " | " | —CONHCH(CH₃)₂ | 171 |
| 122 | " | " | " | " | —CONHCH₂C(CH₃)₃ | 165-9 |
| 123 | C₂H₅ | " | " | " | —COOLi | 278-83 |
| 124 | " | " | " | " | —COOCH(CF₃)₂ | oil |
| 125 | " | " | " | " | —COOCH₂CF₂CHFCF₃ | oil |
| 126 | " | " | " | " | —CON(CH₃)CH₂CH(OCH₃)₂ | oil |
| 127 | " | " | " | " | —CONHCH₂CH(OC₂H₅)₂ | 158-60 |
| 128 | " | " | " | " | —CONHC₃H₇ | 176-80 |
| 129 | " | " | " | " | —CON(CH(CH₃)₂)₂ | oil |
| 130 | " | " | " | " | —CONHCH₂OC₂H₅ | 85-88 |
| 131 | " | " | " | " | —CONHCH₂OCH₃ | |
| 132 | " | " | " | " | —CONHCH₂OC₃H₇ | |
| 133 | " | " | Br | " | —COOK | >250 |
| 134 | " | " | " | " | —CONH₂ | 211-3 |
| 135 | " | " | " | " | —CONHCH₂CH(OCH₃)₂ | 98-101 |
| 136 | " | " | Cl | 5-Cl | —COOK | >270 |
| 137 | " | " | " | " | —COOCH(CH₃)₂ | 80-4 |
| 138 | " | " | " | " | —COOC₃H₇ | oil |
| 139 | " | " | " | " | —COSC₄H₉ | oil |
| 140 | " | " | " | " | —CONHCH₃ | 190-5 |
| 141 | " | " | " | " | —CON(C₂H₅)₂ | 92-7 |
| 142 | " | " | " | 4-CH₃ | —COONa | >300 |
| 143 | " | " | " | " | —COOK | 214-6 |
| 144 | " | " | " | " | —COOHN(CH₂CH₂OH)₃ (⊖⊕) | 120-2 |
| 145 | " | C₂H₅ | " | " | —COOCH(CH₃)₂ | 92-5 |
| 146 | " | " | " | " | —COOC₄H₉ | oil |
| 147 | " | " | " | " | —COOCH₂CF₃ | oil |
| 148 | " | " | " | " | —COOCH₂—CH=CH₂ | oil |
| 149 | " | " | " | " | —CONHCH₃ | 186-8 |
| 150 | " | " | " | " | —CON(CH₃)₂ | oil |
| 151 | " | " | " | " | —CONHC₂H₅ | 146-7 |
| 152 | " | " | " | " | —CONHCH(CH₃)₂ | 146-8 |
| 153 | " | " | " | " | —CONHCH₂—CH(CH₃)₂ | 192-4 |
| 154 | " | " | " | " | —CONH(CH₂)₃OCH₃ | 122-4 |
| 155 | " | " | " | " | —CONHCH₂CH(OC₂H₅)₂ | 139-40 |
| 156 | " | CH₃ | " | H | —COOK | resin |
| 157 | " | " | " | " | —COOCH₂CF₃ | oil |
| 158 | " | " | " | " | —COOC₄H₉ | oil |
| 159 | " | " | " | " | —COOCH₂CH₂OCH₃ | oil |
| 160 | " | " | " | " | —CONHCH₃ | resin |
| 161 | " | " | " | " | —CONHCH₂CH(CH₃)₂ | 150-9 |
| 162 | " | " | " | " | —CONHCH₂CH(OCH₃)₂ | 115-9 |

BIOLOGICAL EXAMPLES

1. Inhibition of growth in cereals

In dish experiments in a greenhouse, young cereal plants (wheat, barley and rye) at the 3-leaf stage were sprayed until dripping wet with compounds according to the invention and with a comparison compound from DE-A No. 3,217,094 at various active ingredient concentrations (kg/ha).

When the untreated control plants had reached a growth height of about 55 cm, the growth in all the plants was measured, and the growth inhibition calculated in % of the control plant growth. In addition, the phytotoxic effect of the compounds was observed. The growth inhibition was determined as a percentage value, 100% denoting cessation of growth and 0% denoting growth corresponding to the untreated control plants. It became apparent that the compounds have very good growth-regulating properties.

The results are collated in Table 2 below.

TABLE 2

| Compound according to Example No. | Dose (kg of a.i./ha) | Growth inhibition (%) | | | Phytotoxic effect |
|---|---|---|---|---|---|
| | | wheat | barley | rye | |
| 39 | 2.5 | 27 | 35 | 27 | no |
| | 1.25 | 22 | 27 | 25 | damage |
| | 0.62 | 18 | 19 | 18 | |
| 40 | 2.5 | 29 | 35 | 27 | no |

TABLE 2-continued

| Compound according to Example No. | Dose (kg of a.i./ha) | Growth inhibition (%) wheat | barley | rye | Phytotoxic effect |
|---|---|---|---|---|---|
| | 1.25 | 23 | 26 | 24 | damage |
| | 0.62 | 18 | 19 | 18 | |
| 51 | 2.5 | 25 | 36 | 18 | no |
| | 1.25 | 10 | 31 | 11 | damage |
| | 0.62 | 5 | 23 | 5 | |
| 54 | 2.5 | 21 | 25 | 19 | no |
| | 1.25 | 14 | 17 | 16 | damage |
| | 0.62 | 7 | 11 | 10 | |
| 64 | 2.5 | 19 | 37 | 19 | no |
| | 1.25 | 16 | 30 | 10 | damage |
| | 0.62 | 11 | 24 | 4 | |
| 77 | 2.5 | 26 | 34 | 27 | no |
| | 1.25 | 24 | 29 | 20 | damage |
| | 0.62 | 19 | 23 | 18 | |
| 81 | 2.5 | 28 | 36 | 27 | no |
| | 1.25 | 24 | 28 | 24 | damage |
| | 0.62 | 19 | 20 | 19 | |
| 91 | 2.5 | 25 | 32 | 28 | no |
| | 1.25 | 17 | 28 | 25 | damage |
| | 0.62 | 11 | 19 | 17 | |
| 127 | 2.5 | 21 | 26 | 19 | no |
| | 1.25 | 13 | 19 | 15 | damage |
| | 0.62 | 7 | 12 | 7 | |
| 130 | 2.5 | 22 | 29 | 10 | no |
| | 1.25 | 15 | 24 | 14 | damage |
| | 0.62 | 9 | 16 | 8 | |
| 133 | 2.5 | 28 | 35 | 26 | no |
| | 1.25 | 22 | 26 | 21 | damage |
| | 0.62 | 18 | 21 | 17 | |
| 147 | 2.5 | 26 | 33 | 21 | no |
| | 1.25 | 18 | 24 | 15 | damage |
| | 0.62 | 12 | 11 | 9 | |

2. Growth inhibition in paddy rice

Rice plants were raised and, at the stage of maximum tillering, treated with the compounds according to the invention and with a comparison compound from DE-A No. 3,217,094. The substances were applied both by spraying and by direct addition to the water.

The growth in all plants was measured three weeks after treatment, and the growth inhibition calculated in % of the control plant growth. In addition, a possible phytotoxic effect of the compound was looked for.

The results are collated in the table below.

TABLE 3

| Compound according to Example No. | Dose (kg/ha) | Growth inhibition (%) | Phytotoxic effect |
|---|---|---|---|
| 39 | 2.5 | 43 | no |
| | 1.25 | 41 | damage |
| | 0.62 | 33 | |
| 40 | 2.5 | 44 | no |
| | 1.25 | 39 | damage |
| | 0.62 | 31 | |
| 51 | 2.5 | 30 | no |
| | 1.25 | 23 | damage |
| | 0.62 | 15 | |
| 54 | 2.5 | 32 | no |
| | 1.25 | 25 | damage |
| | 0.62 | 17 | |
| 64 | 2.5 | 31 | no |
| | 1.25 | 23 | damage |
| | 0.62 | 17 | |
| 77 | 2.5 | 40 | no |
| | 1.25 | 35 | damage |
| | 0.62 | 29 | |
| 81 | 2.5 | 46 | no |
| | 1.25 | 41 | damage |
| | 0.62 | 35 | |
| 91 | 2.5 | 42 | no |
| | 1.25 | 37 | damage |
| | 0.62 | 29 | |
| 127 | 2.5 | 31 | no |
| | 1.25 | 24 | damage |
| | 0.62 | 17 | |
| 130 | 2.5 | 36 | no |
| | 1.25 | 25 | damage |
| | 0.62 | 19 | |
| 147 | 2.5 | 33 | no |
| | 1.25 | 25 | damage |
| | 0.62 | 19 | |

We claim:

1. A compound of the formula I

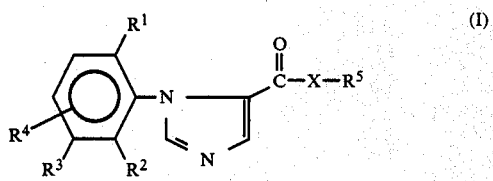

in which
$R^1$ and $R^2$, independently of one another, are $(C_1-C_4)$-alkyl,
$R^3$ is halogen,
$R^4$ is hydrogen, Cl, Br or methyl,
X is O, S or $N-R^5$, and
$R^5$ is hydrogen, $(C_2-C_6)$-alkenyl or $(C_1-C_6)$-alkyl, where the alkyl group may be up to disubstituted by $(C_1-C_6)$-alkoxy or $(C_1-C_3)$-dialkylamino, or up to hexasubstituted by halogen, or an agriculturally suitable salt thereof
with the proviso that $R^3$ is not Cl when $R^1$ and $R^2$ are each $CH_3$ and $R^4$ is hydrogen.

2. A plant-growth regulator, which consisting essentially of an effective amount of a compound of the formula (I) of claim 1, or a salt thereof, and a conventional carrier therefore.

3. A method for regulating the growth of plants, wherein an effective amount of a compound of the formula (I) of claim 1, or a salt thereof, is applied to the plants or the cultivated areas.

4. A compound as claimed in claim 1, wherein $R^1$ is $C_2H_5$, $R^2$ is $C_2H_5$, $R^3$ is Cl, $R^4$ is H, X is O and $R^5$ is $C_2H_5$.

* * * * *